United States Patent [19]

Hu et al.

[11] Patent Number: 5,396,528
[45] Date of Patent: Mar. 7, 1995

[54] TOMOGRAPHIC IMAGE RECONSTRUCTION USING CROSS-PLANE RAYS

[75] Inventors: Hui Hu, Waukesha; Carl R. Crawford, Milwaukee; Armin H. Pfoh, New Berlin; Jiang Hsieh, Waukesha, all of Wis.

[73] Assignee: General Electric Company, Milwaukee, Wis.

[21] Appl. No.: 723,361

[22] Filed: Jun. 28, 1991

[51] Int. Cl.$^6$ .......................................... G01N 23/083
[52] U.S. Cl. .................................. 378/14; 378/901; 364/413.18; 364/413.16
[58] Field of Search ...................... 364/413.13, 413.14, 364/413.16, 413.18; 378/4, 14, 19, 901

[56] References Cited

U.S. PATENT DOCUMENTS

| | | | |
|---|---|---|---|
| 4,086,492 | 4/1978 | Lodge et al. | 250/416 |
| 4,138,721 | 2/1979 | Boyd | 364/414 |
| 4,293,912 | 10/1981 | Walters | 364/414 |
| 4,309,615 | 1/1982 | Kowalski | 250/445 T |
| 4,352,021 | 9/1982 | Boyd et al. | 378/12 |
| 4,442,489 | 4/1984 | Wagner | 364/414 |
| 4,888,693 | 12/1989 | Tam | 364/413.16 |
| 4,965,726 | 10/1990 | Heuscher et al. | 364/413.19 |
| 5,053,958 | 10/1991 | Tam | 364/413.13 |
| 5,216,601 | 6/1993 | Crawford et al. | 364/413.16 |
| 5,228,069 | 7/1993 | Arenson et al. | 378/19 |

FOREIGN PATENT DOCUMENTS

| | | |
|---|---|---|
| 0389333 | 9/1990 | European Pat. Off. . |
| 2-51788 | 1/1988 | Japan . |
| 63-2607 | 2/1990 | Japan . |
| 2088670 | 6/1982 | United Kingdom . |

OTHER PUBLICATIONS

Iteractive Three-Dimensional Reconstruction From Twin-Cone Beam Projections, M. Schlindwein, IEEE Trans. on Nuclear Science vol. NS-25, No. 5, Oct. 1978.

The Theory of Three-Dimensional Image Reconstruction for PET, J. G. Rogers, et al., IEEE Transactions on Medical Imaging, vol. MI-6, No. 3, Sep. 1987.

Primary Examiner—Paul M. Dzierzynski
Assistant Examiner—David V. Bruce
Attorney, Agent, or Firm—Quarles & Brady

[57] ABSTRACT

A CT apparatus employing a cone beam of x-rays reduces image artifacts by employing full as opposed to half scans of less than 360°. The present invention recognizes that rays of a cone beam that cross the imaging plane are not redundant with opposing rays in the scan, as is the case with the rays within the imaging plane. In a second embodiment, half scans of less than 360° are obtained using in-plane and cross-plane rays of the cone beam and the data from the in-plane rays is used to estimate the missing data from that collected with the cross-plane rays.

3 Claims, 4 Drawing Sheets

FIG. 6
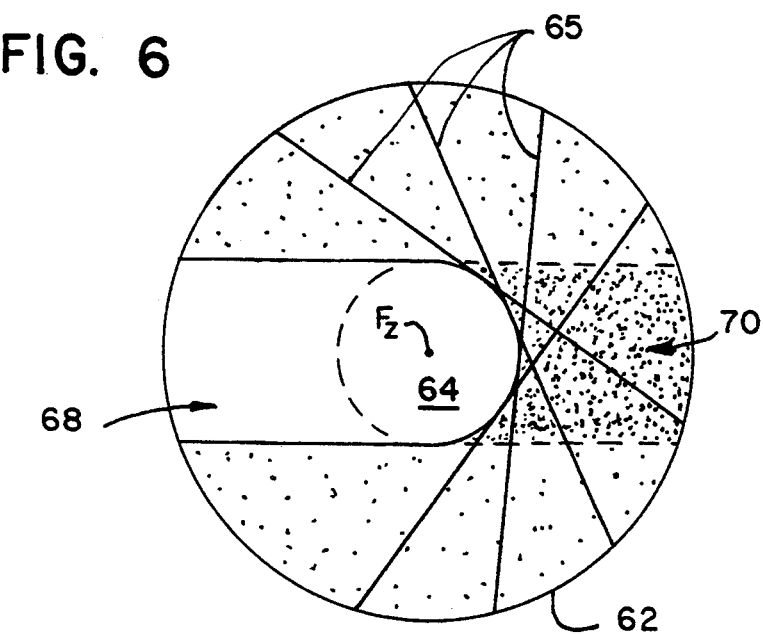
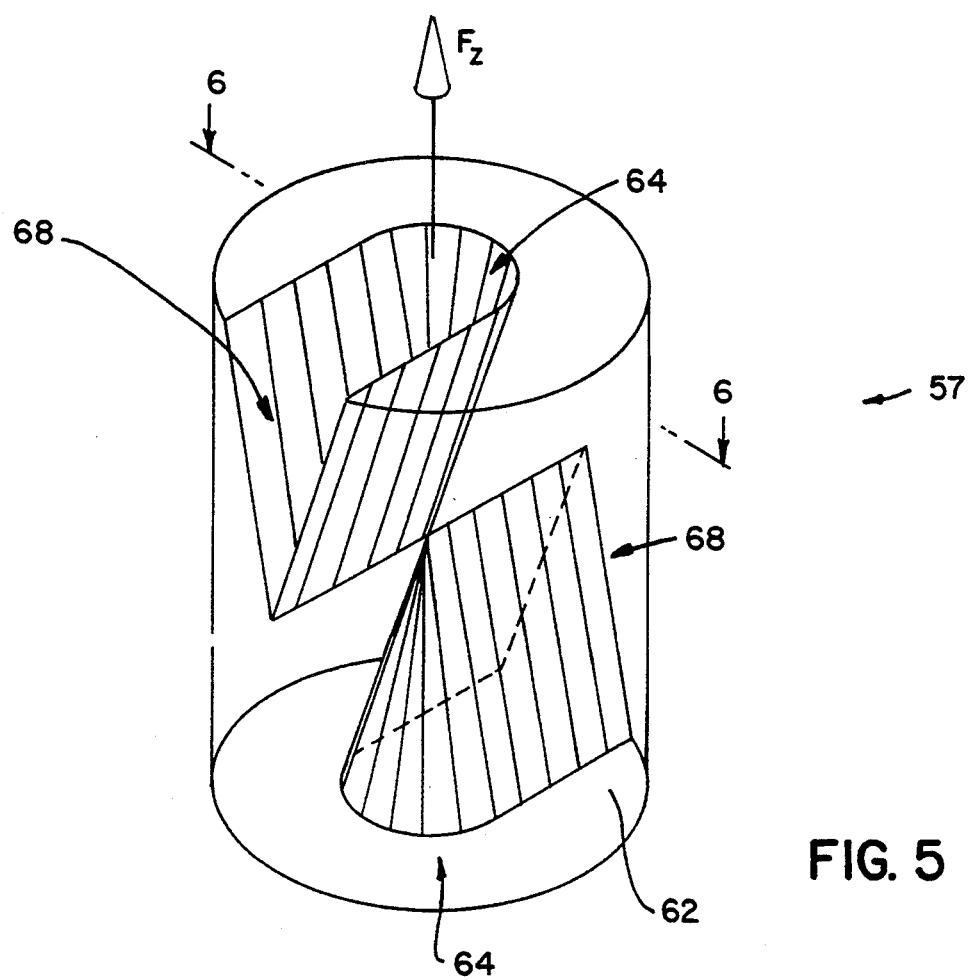
FIG. 5

TOMOGRAPHIC IMAGE RECONSTRUCTION USING CROSS-PLANE RAYS

BACKGROUND OF THE INVENTION

This invention relates to computed tomography (CT) systems and specifically to CT systems in which projections of the imaged object are taken both along rays within the gantry plane and rays crossing the gantry plane.

In a typical computed tomography system, an x-ray source, mounted to a rotating gantry, is collimated to form a fan beam with a defined fan beam angle. The fan beam is typically oriented to lie within the "gantry plane", a plane normal to the axis of rotation of the gantry, and is transmitted through an imaged object to an x-ray detector array also oriented within the gantry plane. The axis of rotation of the gantry is also referred to as the z-axis.

The detector array is comprised of a line of detector elements, each of which measures the intensity of transmitted radiation along a ray projected from the x-ray source to the particular detector element. The intensity of the transmitted radiation is dependent on the attenuation of the x-ray beam along that ray by the imaged object.

The x-ray source and detector array may be rotated on the gantry within the gantry plane and around a center of rotation so that the "gantry angle" at which the fan beam axis intersects the imaged object may be changed. At each gantry angle, a projection is acquired comprised of the collected intensity signals from each detector element. The gantry is then rotated to a new angle and the process is repeated to collect projections data along a number of gantry angles to form a tomographic projection set.

Often, $2\pi$ radians or 360° of gantry rotation will be used to collect the projection set; however, for fan beam CT systems, it has been determined that a mathematically complete projection set may be obtained with as little as $\pi$ radians, plus the angle of the fan beam of gantry rotation. The use of less than $2\pi$ radians of gantry rotation to collect a projection set will be referred to generally as "half scan".

The acquired tomographic projection sets are typically stored in numerical form for later computer processing to "reconstruct" a slice image according to reconstruction algorithms known in the art. A projection set of fan beam projections may be reconstructed directly into an image by means of fan beam reconstruction techniques, or the intensity data of the projections may be sorted into parallel beams and reconstructed according to parallel beam reconstruction techniques. The reconstructed tomographic images may be displayed on a conventional CRT tube or may be converted to a film record by means of a computer controlled camera.

A typical computed tomographic study involves the acquisition of a series of "slices" of an imaged object, each slice parallel to the gantry plane and having a slice thickness dictated by the size of the focal spot, the width of the detector array, the collimation, and the geometry of the system. Each successive slice is displaced incrementally along a z-axis, perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, a growing number of slices are required in the z-dimension. The time and expense of a tomographic study increases with the number of sequential slices required. Also, the longer scan times necessary to acquire more slices increases the discomfort to the patient who must remain nearly motionless to preserve the fidelity of the tomographic reconstructions. Accordingly, there is considerable interest in reducing the time required to obtain a slice series.

One method of decreasing the scanning time needed to collect multiple slices of data is to acquire projection data for more than one slice during a given gantry rotation. This may be done by using a two-dimensional detector array extending along the z-axis to obtain projection data on either side of the gantry plane, and by changing the collimation of the x-rays from that of a fan beam to, for example, a cone beam having rays diverging from a focal spot not only within the gantry plane but to either side of the gantry plane as well. It will be recognized that such a cone beam generally need not be a true cone but may also include, for example, pyramidal dispersions of x-rays in three dimensions. The collection of radiation from more than a single plane during one projection will be referred to generally as three dimensional scanning.

Despite the potential advantages of three-dimensional scanning, the images are frequently degraded by artifacts which obscure structures within the imaged object.

SUMMARY OF THE INVENTION

The present invention is based on the discovery of the source of certain of the image artifacts produced by cone beam systems and provides two means for eliminating these artifacts.

Specifically, in a first embodiment, a two-dimensional detector array collects radiation along first, in-plane rays passing through the imaged object perpendicular to the axis of rotation of the gantry and along second, cross-plane rays passing through the imaged object but not perpendicular to that axis. The detector array produces first and second signals indicating the intensities of the first and second rays respectively. The gantry to which the detector array is attached is rotated to move the detector array in an orbit about the axis, and the imaged object, over an angular range equaling an integer multiple of $2\pi$ radians. The first and second signals obtained within this angular range form the projection set.

It is one object of the invention to eliminate certain image artifacts caused by the use of cross-plane rays in conjunction with half scanning. It has been determined that, unlike with in-plane rays, in half scanning with cross-plane rays, critical projection information is lost. This information is recaptured only by ensuring that the projection set is taken over $2\pi$ radians of gantry rotation.

In a second embodiment, two dimensions of projection information are collected in a half scan over a range of gantry angles less than $2\pi$ radians, and for a number of positions along the z-axis, by rotating the detector array around the axis and translating in-plane and cross-plane rays along the axis. The first and second signals from the detector array produce a first and second data set respectively. The first data set is then used to estimate values for second data, at gantry angles not within the range of measured gantry angles; to produce a third data set, the second and third are combined, and the combined data set is reconstructed with the first data set to produce an image set.

Thus it is another object of the invention to allow the cross-plane rays to augment the information obtained from the in-plane rays when half scanning is desired and yet to reduce the image artifacts that would result from a simple combining of the two sets of data. The third data set forms an estimate of the missing data from the second data set, such missing data being the source of the artifacts.

The estimation process may be performed by reconstructing the first data to a three-dimensional image matrix and re-projecting this image matrix along the cross-plane rays for each z-axis position, and at gantry angles not within the range of measured gantry angles to produce the third data set.

It is thus another object of the invention to provide a simple means of estimating the missing data of the second data set without the need for complicated splicing and weighting procedures.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 5 is a diagram of the three dimension Fourier space of FIG. 4 for half scans, with cross-plane rays, over less than $2\pi$ radians showing the asymmetric data loss which causes image artifacts in the reconstructed image;

FIG. 6 is a cross-section of the three dimension Fourier space of FIG. 5 showing the areas of missing and redundant data collected in a scan of less than $2\pi$ radians.

DETAILED DESCRIPTION OF THE PREFERRED EMBODIMENT

Figure 1:
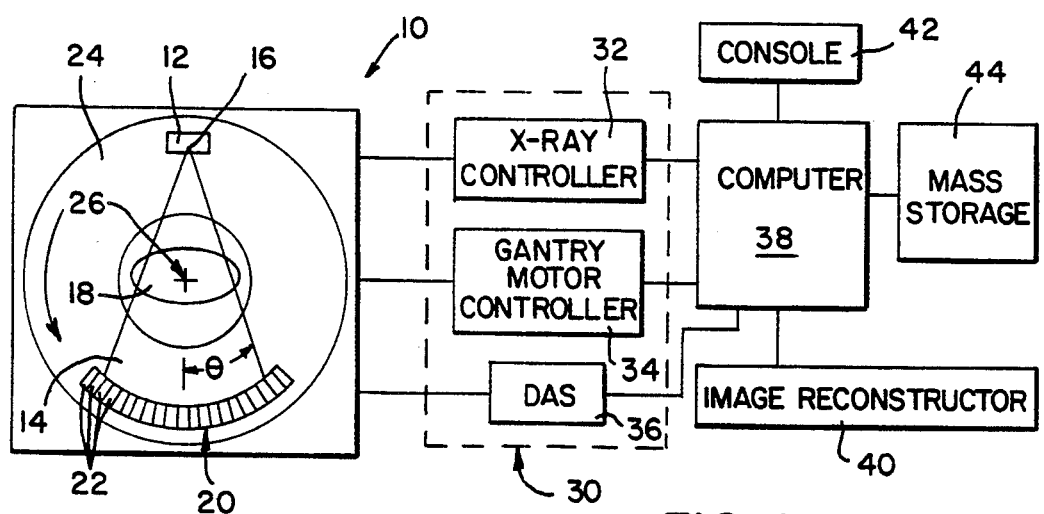
FIG. 1 is a schematic representation of a CT system, as may be used with the present invention, including a gantry holding an x-ray source and x-ray detector for obtaining projections of a patient.
Figure 2:
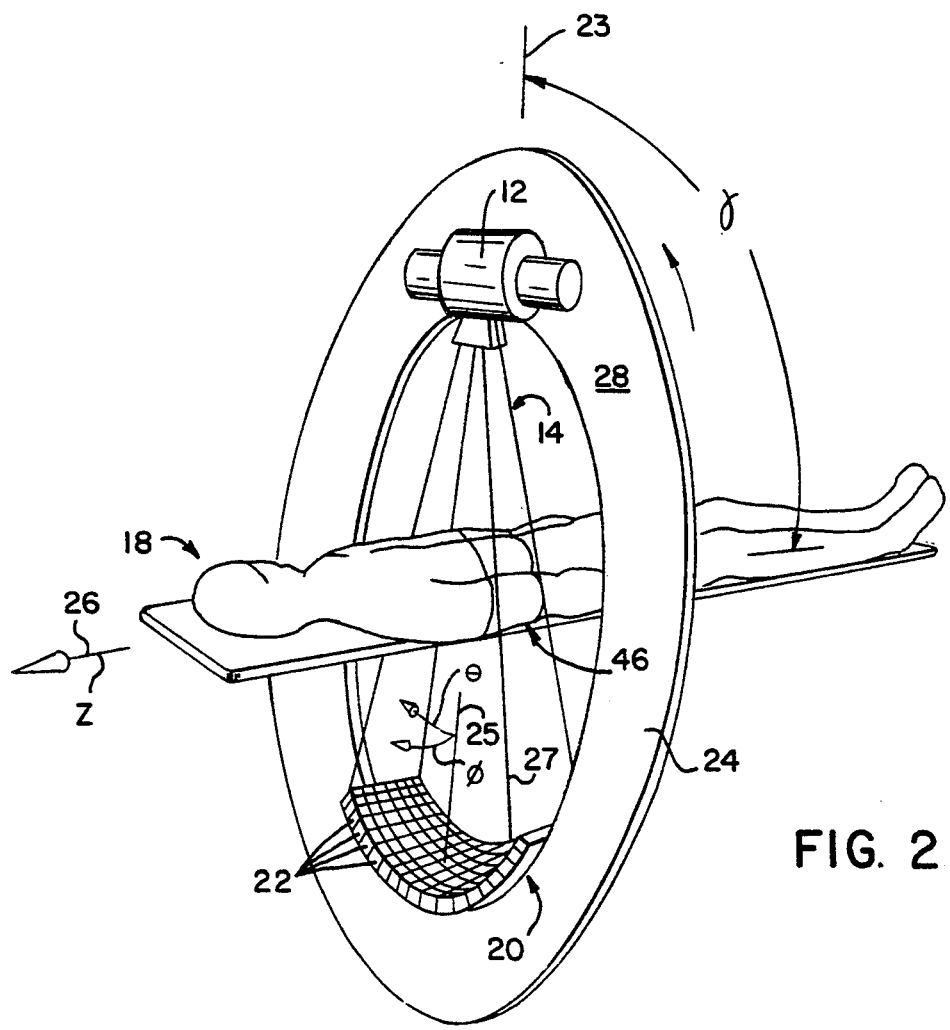
FIG. 2 is a simplified perspective view of the gantry of FIG. 1 showing the cone beam of x-rays from the x-rays source and the two-dimensional detector array suitable for three dimensional scanning.

Referring to FIGS. 1 and 2, a CT system 10 representative of a three-dimensional CT scanner includes an x-ray source 12 oriented to project a cone beam of x-rays 14 from a focal spot 16 through a patient 18 to be received by a two-dimensional detector array 20.

The two-dimensional detector array 20 is comprised of a number of detector elements 22 arranged over the area of the detector array 20 in generally perpendicular columns and rows together to detect a projected image from the transmission of the x-rays 14 through the patient 18.

The x-ray source 12 and the two-dimensional detector array 20 are mounted on either side of a gantry 24 so as to rotate in opposition about an axis of rotation 26 generally positioned within the patient 18. The axis of rotation 26 forms the z-axis of a Cartesian coordinate system generally having its origin centered within the cone beam 14. The plane defined by the x and y axes of this coordinate system thus defines a plane of rotation, specifically the gantry plane 28 of the gantry 24.

Rotation of the gantry 24 is measured by angle $\gamma$ from an arbitrary reference position within the gantry plane 28. Angle $\gamma$ varies between 0 and $2\pi$ radians (360°).

The x-rays of the cone beam 14 diverge from the gantry plane 28 by angle $\phi$ and diverge along the gantry plane 28 by angle $\Theta$. Correspondingly, the two-dimensional detector array 20, is arranged generally as a section of the surface of a sphere having a center at the focal spot 16, and has its grid of detector elements 22 arranged so as to receive and make intensity measurements along the rays of the cone beam 14 throughout the angles of $\phi$ and $\Theta$ of the cone beam 14. Rays 25 of the cone beam 14 having values of $\phi=0$, lie in the gantry plane 28 and will be termed "in-plane rays". The in-plane rays 25 are those rays used in conventional fan beam CT systems. Those rays 27 having values of $\phi \neq 0$ will be termed "cross-plane rays".

Referring to FIG. 1, the control system of the CT scanner 10 has gantry associated control modules 30 which include: x-ray controller 32, which provides power and timing signals to the x-ray source 12, gantry motor controller 34, which controls the rotational speed and position of the gantry 24, and data acquisition system (DAS) 36, which receives projection data from the two-dimensional detector array 20 and converts the data into digital words for later computer processing preserving also the values of $\phi, \Theta$ and the gantry angle $\gamma$ at which the data was taken. The x-ray controller 32, the gantry motor controller 34 and the data acquisition system 36 are connected to computer 38 for control by computer 38 and to transmit data to computer 38.

The computer 38 is a general purpose mini-computer and may be programmed to acquire and manipulate projection data per the present invention as will be described in detail below. The computer 38 is connected to an image reconstructor 40 which performs high speed image reconstruction according to methods known in the art. The image reconstructor 40 is an array processor. The computer 38 receives commands and scanning parameters via operator console 42 which is generally a CRT display and keyboard which allow an operator to enter parameters for the CT scan and to display the reconstructed image or other information from computer 38. A mass storage device 44 provides a means for storing operating programs for the CT imaging system 10 as well as storing projection and image data for future reference by the operator.

Figure 3:
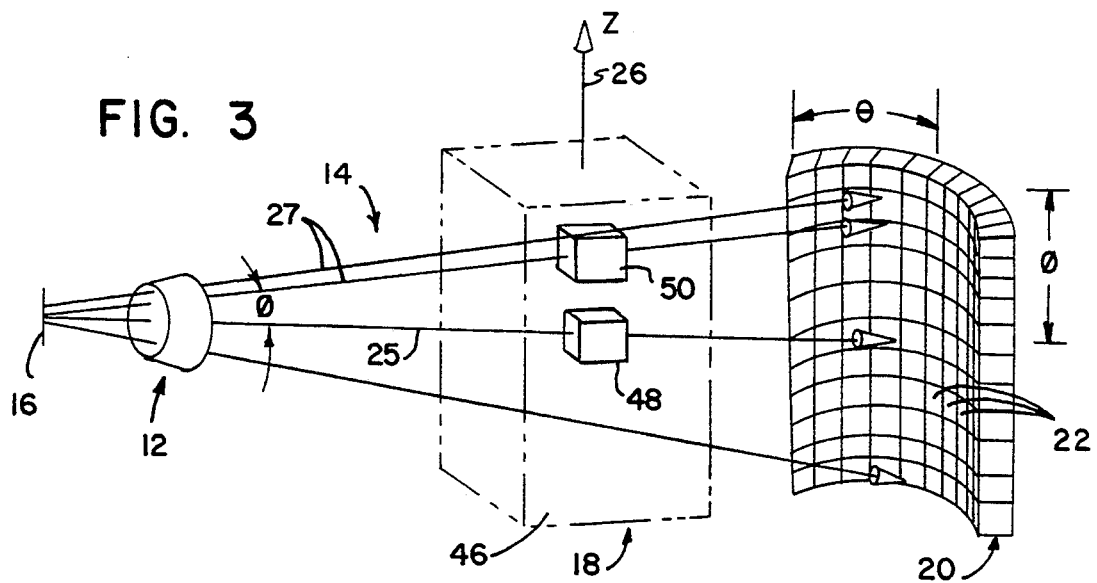
FIG. 3 is a geometric representation of a volume of the patient as illuminated by the cone beam of x-rays showing the parallelism of cross-plane rays for small subvolumes.

Referring to FIG. 3, for a given projection, the cone beam of x-rays 14 strikes a volume 46 of the patient 18. Within that volume 46, a first subvolume 48 receives in-plane rays 25 from the cone beam 14 having a $\phi$ value of zero. These in-plane rays 25 are detected by the detector elements 22 of the two-dimensional detector array 20 within the gantry plane 28 (shown in FIG. 2) along a single row within the gantry plane 28. A second subvolume 50, displaced along the z-axis from the first subvolume 48, receives cross-plane rays 27 having $\phi$ values not equal to zero. These cross-plane rays 27 are detected by other rows of detector elements 22 of the two-dimensional detector array 20, such rows not lying within the gantry plane 28.

Provided subvolume 50 is small, the cross-plane rays 27 intercepting subvolume 50 are essentially parallel to each other.

Figure 4:
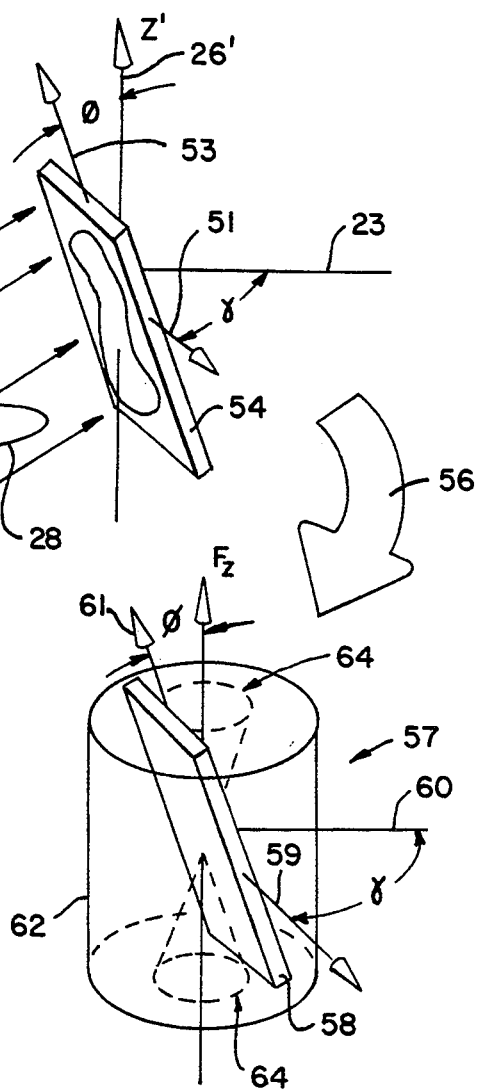
FIG. 4 is a diagrammatic representation of the Three Dimensional Fourier Slice Theorem showing the generation of Fourier space data from multiple projections of cross-axis rays.

Referring to FIG. 4, during scanning an object 52 within sub-volume 50 is illuminated by essentially parallel cross-plane rays 27 to create a parallel, two-dimensional projection 54. The plane of projection 54 is perpendicular to the cross-plane rays 27 i.e. the normal to the plane 54 is parallel to rays 27, and is centered on a Z'-axis 26' parallel to Z-axis 26. The Three Dimensional Fourier Slice Theorem states that the two-dimensional Fourier transform of a two-dimensional parallel projection of an object provides the values of three-dimensional Fourier transform of the object in a corresponding radial plane in Fourier space, where the normal to the corresponding radial plane in Fourier space plane is parallel to the direction of the projection. Accordingly, the two-dimensional parallel projection 54, when operated on by a two-dimensional Fourier transform 56 provides a similar plane 58 of data in Fourier space 57.

The two-dimensional projection 54 has a first axis 51 perpendicular to the Z'-axis 26' and a second axis 53 tipped with respect to the Z-'axis 26' by angle $\phi$ so as to receive the cross-plane rays 27 of the cone beam 14 perpendicularly to its surface. The first axis 51 of the two-dimensional projection 54 is rotated around the Z'-axis 26' by an amount $\gamma$ from reference angle 23 determined by the position of the gantry 24, as previously described.

Similarly, by the above theorem, the two-dimensional Fourier transform 56 of the two-dimensional projection 54 yields the values of the three-dimensional Fourier transform of the object 52 in Fourier space 57 along a plane 58 having a first axis 59 rotated by angle $\gamma$ around perpendicular Fourier space axis $F_z$ with respect to a reference 60, and a second axis 63 rotated by angle $\phi$ with respect to $F_z$. The axis $F_z$ is simply a Cartesian coordinate axis of Fourier space 57 defined as corresponding to the Z-axis 26.

For different projections 54 obtained at different angles $\gamma$ by rotation of gantry 24, additional planes 58 of Fourier data will be obtained. Each plane 58 of Fourier data will have same angle $\phi$ with respect to $F_z$, as fixed by the angle $\phi$ of the cross-plane rays 27, but will be rotated around $F_z$ so as to sweep out a cylinder of data 62 in Fourier space 56 excluding two conical areas 64. The excluded conical areas 64 are cones having bases abutting the bases of the cylinder 62 and vertices meeting at the centerpoint of cylinder 62. The vertex angle of these conical areas 64 is equal to $2\phi$, and thus the conical areas grow larger as the $\phi$ value of the cross-plane rays 27 increases. The cylinder 62 and the cones 64 bound the data obtained in Fourier space for projections 54 taken at angles of $\gamma$ ranging over $2\pi$ radians during rotation of the gantry 24.

Reconstruction of an image of the object 52 requires taking the inverse Fourier transform of the data of cylinder 62. Generally this inverse Fourier transform is taken along a single plane through cylinder 62 so as to produce a tomographic or slice image.

The effect of the missing data of the conical areas 64 on the reconstructed image is to eliminate low spatial frequencies from the reconstructed image. Provided the angles $\phi$ of the cross-plane range 27 are low, however, such loss of low frequency information, although not desirable, may be tolerated for many imaging applications.

When three-dimensional scanning is used with half scanning techniques, in which the gantry 24 does not rotate by $2\pi$ radians, but by a lesser amount on the order of $\pi$ radians, the data 62 collected by the cross-plane rays 27 will exhibit a much more pronounced shortfall.

Referring to FIG. 5, in a half scan with cross-plane rays 27, data will be lost from the cylinder 62 along v-shaped channels 68 proceeding radially out from the axis $F_z$ in opposite directions for each cone 64. Thus, unlike the case of in-plane rays 25, where no significant data is lost from the Fourier space 57 for a half scan, in the case of cross-plane rays 27, the use of half scans will cause significant data loss in the Fourier space 57. In particular, the lost data of channels 68 includes high frequency components of the reconstructed image asymmetrically disposed about the axis $F_z$ and thus creates ghost artifacts that may obscure important detail in the reconstructed image.

In summary, and referring also to FIG. 6, for a given plane of FIG. 5 along the $F_x$ and $F_y$ axes, orthogonal to $F_z$ in the Fourier space 57, data will be lost within the conical area 64 and v-shaped channel 68. Important also, however, in the area at 70 directly opposite the v-shaped channel 68 reflected about the axis $F_z$, the cross-axis beams 27 provide redundant data. That is, the area 70 is swept twice by the rotating plane 58. This non-uniform data sampling contributes to image artifacts.

The sweeping of the cylinder 62 in Fourier space 57, by the canted plane 58 along the cross section of FIG. 6, can be visualized by imagining the movement of a line 65 tangent to the circle forming the cross section of conical area 64 in that cross-section, as that point of tangency moves around the circle with changing $\gamma$.

The image artifacts identified to the use of cross-plane rays 27 with half scanning techniques may thus be eliminated by insuring that a full scan of $2\pi$ radians of gantry rotation is taken if cross-plane rays 27 are used. In this case, the missing data will be confined to the radially symmetrical cones 64 whose volumes may be limited by limitation of the angle $\phi$ of the cross plane rays 27.

In a second embodiment, the cross-plane rays 27 of the cone beam 14 may be used to supplement the information obtained by the in-plane rays 25 of the cone beam 14. In this embodiment every sub-volume 50 and 48 (shown in FIG. 3) is half scanned both by cross-plane rays 27 and by in-plane rays 25. The in-plane rays 25 may produce a complete set of image data with a half scan of gantry rotation. Nevertheless, as described above, image artifacts will result if the projection data from the cross-plane rays 27 is combined with the projection data from the in-plane rays 25 because of the missing data of the cross-plane range as shown in FIG. 5.

However, provided each sub-volume 48 and 50 is scanned both by cross-plane and in-plane rays 27 and 25, the image artifacts may be reduced by using the projection data from the in-plane rays 25 to estimate values for these missing data obtained from the cross-plane rays 27.

Referring to FIGS. 1, 2 and 3, the half scanning is performed by first positioning the patient 18, and hence the volume 46, along the z-axis at a first position. The gantry 24 is then rotated throughout a half scan angular range of less than $2\pi$, while data for the in-plane rays 25 and the cross-plane rays 27 is acquired at discrete angular intervals. At the conclusion of the rotation of the gantry 24 through this angular range, the patient 18 is translated to a second position along the z-axis 26 and the gantry 24 is again rotated through its half scan while data is again collected for in-plane rays 25 and the cross-plane rays 27 at discrete angular intervals.

Typically the data for each z-axis position in the half scan is obtained by rotating the gantry 24 over a range of $\pi$ radians $+2\phi$, the cone beam angle, in between translations of the volume 46 along the z-axis 26.

Figure 7:
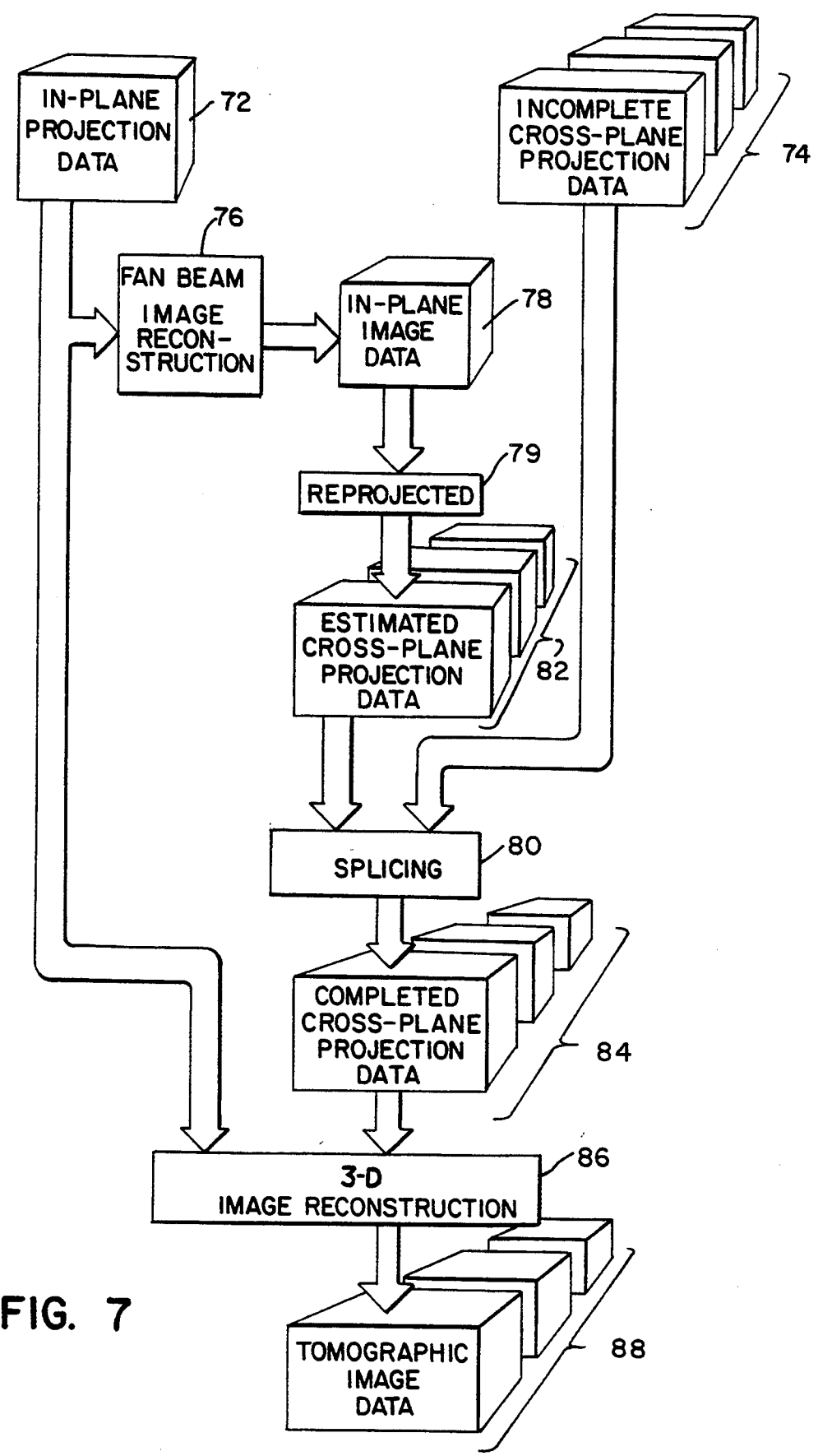
FIG. 7 is a block diagram of a process of the present invention for estimating the lost data of cross-plane rays in a half scan from the reprojection of in-plane data from that half scan.

Referring to FIGS. 7 and 3, the half scanned data for the cross-plane ray 27, produces incomplete cross-plane projection data 74, and the half scanned data for the in-plane rays 25 produces in-plane projection data 72. Projection data 72 produces a single three dimensional array of projection data points corresponding to the projections of the in-plane rays 25 as received by a single row of detector elements 20 for each gantry angle $\gamma$ and for each z-axis position. The collected projection data 74 comprises multiple three dimensional arrays of data, one corresponding to each row of detector elements 20 outside of the gantry plane 28 as identified by different angles $\phi$ of the received cross-plane rays 27.

Projection data 72 from the in-plane rays 25 is reconstructed, by well known fan beam reconstruction techniques, as indicated by process block 76 to produce in-plane image data 78 for the volume 46. As is understood in the art, the image data 78 consists of a matrix of values, each representing the x-ray absorptivity of a volume element of the patient 18 within the volume 46.

This image data 78 is then re-projected mathematically, as indicated by process block 79, along the cross-plane rays 27 for gantry angles $\gamma$ beyond the range of the half scan. For example, if the half scan is over gantry angles $\gamma$ from 0 to $\pi$ radians $+2\phi$, the re-projecting occurs from the values $\pi$ radians $+2\phi$ to $2\pi$ radians. The process of re-projecting 79 is well understood in the art and involves summing the values of the image data 78 along lines through the matrix corresponding to the cross-plane rays 27 of the cone beam 14. The sums represent the total absorption along those lines and thus create a simulated projection along those rays 27 analogous to the projection that would be obtained from the volume 46 of the patient 18. The re-projecting process 79 produces a new set of estimated cross-plane projection data 82 analogous to the projection data 74, but, as described, covering the gantry angles $\gamma$ beyond those used in the half scan. Thus, projection data 82 and 74 combine to provide an effective $2\pi$ radians of projection data for the cross-plane rays 27 despite the actual half scan.

The projection data 82 and 74 are combined, as shown in process block 80, by splicing the estimated projection data 82 into the array elements of projection data 74, at the sites of previously missing projection data, to produce completed cross-plane projection data 84.

This completed cross-plane projection data 84 is then reconstructed with the in-plane projection data 72 by 3D reconstruction techniques, as indicated by block 86, which incorporates both in-plane and cross-plane rays to produce tomographic image data 88. Tomographic image data 88 may be selectively displayed along planes within its matrix of values as is well understood in the art to produce tomographic images.

Thus, the in-plane projection data 72 may be used to provide the missing data from the cross-plane projection data 74 compensating for the fact that a half scan by cross-plane rays 27 does not provide a complete set of data in Fourier space 57. The combination of the in-plane projection data 72 with the cross-plane projection data 74 improves the signal-to-noise characteristics of the image data 88 over that obtained with the projection data 72 alone. It should be noted that even after this augmentation process, that the conical areas 64 are still missing from the projection data 74. However, as mentioned, the symmetrical low frequency data losses resulting from areas 64 may be tolerated in many applications.

As described above, the data for the v-shaped channel 68 of FIG. 5, missing from the projection data 74, is provided by the expedient of re-projecting an image 78 constructed from the projection data 72 derived from in-plane rays 25. It will be understood to those of ordinary skill in the art, however, from the above description identifying the cause of the artifacts, that other means may be adopted to provide the missing data of the v-shaped channel 68 and to effectively de-weight the redundant data in area 70. For example, corresponding data from set 72 may be removed and spliced into the area 68 of the data set 74. In addition, each of the data values in area 70 may be de-weighted by one-half. Additionally, to prevent artifacts caused by discontinuities between the spliced data from set 72 and the data of sets 74, the boundaries between data within region 68 may be blended to the data outside of region 68 by appropriate weighting schemes.

Many other modifications and variations of the preferred embodiment which will still be within the spirit and scope of the invention will be apparent to those with ordinary skill in the art. For example, the techniques described herein may be applied to other imaging modalities such as position emission tomography where the source of cross-plane and in-plane rays is a decaying isotope within the body or "fourth generation" CT scanning where a stationary detector array receives radiation from an orbiting radiation source. In order to apprise the public of the various embodiments that may fall within the scope of the invention, the following claims are made:

We claim:

1. A method of producing a tomographic image from projection data collected by a two-dimensional detector array receiving radiation along first rays perpendicular to a z-axis and second rays not perpendicular to the z-axis, said detector array producing first and second data indicating the intensities of the first and second rays respectively, comprising the steps of:

a) collecting a first and second projection set comprising first and second projection data, respectively, over a range of gantry angles around the axis of less than $2\pi$ radians and for a number of z-axis positions;

b) estimating from the first projection set, values for the second projection set at the z-axis positions but at gantry angles not within the range of gantry angles, to produce a third projection set;

c) combining the second and third projection sets to produce a completed projection set; and d) reconstructing the completed projection set and the first projection set to produce the tomographic image.

2. The method recited in claim 1 wherein the first rays are received over a fan angle and wherein the range of gantry angles equals $\pi$ radians plus the fan angle.

3. A method as recited in claim 1 wherein step (b) comprises the steps of:

reconstructing the first projection set to a three dimensional image set; and re-projecting the three dimensional image set along the second rays for each z-axis position at gantry angles not within the range of gantry angles to produce the third projection set.

* * * * *